US009066895B2

(12) United States Patent
Chacornac et al.

(10) Patent No.: US 9,066,895 B2
(45) Date of Patent: Jun. 30, 2015

(54) METHOD OF STORING A VACCINE CONTAINING AN ALUMINUM ADJUVANT

(75) Inventors: Isabelle Chacornac, Tupin et Semons (FR); Nabila Ikhelef-Gribi, Francheville (FR); Frédéric Ronzon, Montromant (FR); Julien Tirefort, Lyons (FR); Sandrine Lentsch Graf, Sainte Foy les Lyon (FR)

(73) Assignee: Sanofi Pasteur SA, Lyon (FR)

( * ) Notice: Subject to any disclaimer, the term of this patent is extended or adjusted under 35 U.S.C. 154(b) by 74 days.

(21) Appl. No.: 13/274,714

(22) Filed: Oct. 17, 2011

(65) Prior Publication Data

US 2012/0091026 A1 Apr. 19, 2012

Related U.S. Application Data

(60) Provisional application No. 61/454,248, filed on Mar. 18, 2011.

(30) Foreign Application Priority Data

Oct. 18, 2010 (FR) ..................................... 10 58464

(51) Int. Cl.
*A61K 39/395* (2006.01)
*A61K 39/00* (2006.01)
(52) U.S. Cl.
CPC ........ *A61K 39/00* (2013.01); *A61K 2039/55505* (2013.01)
(58) Field of Classification Search
None
See application file for complete search history.

(56) References Cited

U.S. PATENT DOCUMENTS

| 6,013,264 | A  | * | 1/2000  | Petre et al. ............. 424/227.1 |
| 6,200,627 | B1 |   | 3/2001  | Lubrecht |
| 2055/0158334 |   |   | 7/2005 | Contorni |
| 2007/0253984 | A1 |   | 11/2007 | Khandke et al. |

FOREIGN PATENT DOCUMENTS

| EP | 0 294 127 | 12/1988 |
| WO | 2008/076819 | 6/2008 |

OTHER PUBLICATIONS

Shank-Retlaff et al., "Evaluation of the Thermal Stability of Gardasil," Human Vaccines, vol. 2, No. 4, Jul. 2006, pp. 147-154.

* cited by examiner

*Primary Examiner* — Yunsoo Kim
(74) *Attorney, Agent, or Firm* — Choate, Hall & Stewart LLP; Fangli Chen

(57) ABSTRACT

The invention relates to a method for loading and storing a vaccine composition, containing the antigen adsorbed on the aluminum adjuvant which (a) comprises (i) loading the composition into a container; and (ii) closing the container with a device in particular acting as a stopper, the surface of the device getting into contact with the composition being coated with a fluoropolymer such as Teflon™; and/or (b) loading the composition into a container wherein the inner surface of which is coated with polymerized silicone. The use of fluoropolymer or polymerized silicone optimizes the adsorbed antigen stability upon storage. In a particular embodiment, the antigen is the hepatitis B surface antigen and the aluminum adjuvant is aluminum oxy hydroxide.

13 Claims, No Drawings

METHOD OF STORING A VACCINE CONTAINING AN ALUMINUM ADJUVANT

CROSS-REFERENCE TO RELATED APPLICATIONS

This application claims the benefit of U.S. provisional application 61/454,248, filed Mar. 18, 2011, and French patent application no. 10 58464, filed Oct. 18, 2011. The entire contents of both of these applications are incorporated by reference.

BACKGROUND OF THE INVENTION

1. Field of the Invention

The present invention relates to a method for reducing and/or decelerating the desorption of an antigen that has been adsorbed on an aluminum adjuvant as well as to the product thereof—namely the combination of a vaccine composition comprising the antigen adsorbed on the aluminum adjuvant and a container for the composition, said container having particular characteristics.

2. Summary of the Related Art

A large number of antigens are able to adsorb on an aluminum adjuvant, in particular at neutral pH or at a pH close to neutrality, which is the pH naturally required for compositions that have to be administered to mammals, including humans.

Provided that the amount of adjuvant is such that the antigen can actually adsorb on the adjuvant in an optimum amount when the two compounds are mixed together, the maximum degree of adsorption is very frequently achieved. However, over time, depending on the environmental conditions, the percentage of adsorbed antigen (adsorption rate) may decrease, and this desorption may constitute an instability factor.

Known environmental conditions that can affect the percentage of adsorbed antigen (adsorption rate) include, for example, variations in pH (even slight variations), and the addition of one or more medium component(s) or one or more additional antigen(s) that may compete with the first antigen for the adsorption sites on the adjuvant.

Conventionally, a ready-to-use multi-dose vaccine composition is loaded into vials, e.g., glass vials closed with a plastic stopper. Similarly, a single dose of a vaccine composition may be loaded in a mono-dose vial or a ready-for-injection syringe consisting, in a standard manner, of a reservoir containing the vaccine, a plunger that closes the reservoir at its distal end, and a device for administration, such as a needle attached at its proximal end. According to an alternative standard filling mode, the vaccine dose may also be loaded in a needleless syringe to which the practitioner adds a separately packaged needle at the time of the injection. The reservoir of the syringe is generally made of either glass or plastic and the plunger or the stopper is simply made of plastic, such as a chlorobutyl or bromobutyl polymer, without particular lamination. Standard glass or plastic syringes are sold, for example, by Becton-Dickinson; Gerresheimer A G, Schott A G, Germany; Nuova Ompi srl, Italy; and West Pharma/Daykio. In order to facilitate sliding, the plunger or stopper may have been immersed in a silicone-in-water emulsion so that a silicone film is formed at its surface. Standard plungers/stoppers are sold by Helvoet, Stelmi and West Pharma, for example; some of them already being sold coated with a silicone film (ref. B2 from West Pharma).

Whatever the container used for storage and the device used for closing the container, administration at the time of injection consists of using a syringe and sliding the plunger or the stopper/plunger combination so that the vaccine is delivered.

SUMMARY OF THE INVENTION

We have now found that the material of the container itself as well as that of the device for closing the container can affect the adsorption rate.

We observed that a vaccine composition containing the hepatitis B surface antigen (HBsAg) adjuvanted with an aluminum adjuvant and loaded as a single dose in standard syringe closed with a standard stopper underwent different adsorption rates when stored under identical conditions and for the same period of time (a few days to several months) depending on whether the syringe was stored in the vertical or horizontal position. The same phenomenon has also been seen with vials. The practical consequence of the different storage positions was that the vaccine contained in the reservoirs stored vertically was not in contact with the stopper, whereas there was contact between the composition and the stopper in the horizontally stored reservoirs.

After a certain period of time, the level of adsorption of HBsAg was measured, and we observed that the level of adsorption was much lower for the HBsAg contained in the horizontally-stored reservoirs. This indicated to us that the material of the standard stopper (chlorobutyl or bromobutyl polymer) was responsible for the adsorption decrease.

The solution to this problem is either to prevent contact between the adjuvanted vaccine composition and a stopper made of a material that contributes to decreased adsorption or to use a stopper made of a material that does not contribute to decreased adsorption. In one embodiment, the invention comprises a method and apparatus using a stopper coated with a film of a fluoropolymer, such as Teflon™ or a Teflon™—like substance (such as Omniflex™ from Helvoet Pharma or Fluorotec™ from West Pharma), which decrease or eliminate desorption caused by the stopper.

DETAILED DESCRIPTION OF THE INVENTION

In one aspect, the invention comprises a first method for reducing and/or slowing down the desorption of an antigen initially adsorbed on an aluminum adjuvant during storage, the method comprising (i) loading a container with a vaccine composition containing the antigen initially adsorbed on the aluminum adjuvant; and (ii) closing the container with a device acting as a stopper, the surface of the device contactable with the composition being coated with a fluoropolymer.

In other words, the invention relates to a first method for filling and storing a composition containing the antigen adsorbed on the aluminum adjuvant which comprises (i) filling a container with the vaccine composition; and (ii) closing the container with a device acting as a stopper, the surface of the device contactable with the composition being coated with a fluoropolymer.

In a similar manner, the invention also relates to the use of a device acting as a stopper for closing a container containing a vaccine composition comprising the antigen adsorbed on an aluminum adjuvant, the surface of the device contactable with the composition being coated with a fluoropolymer.

The container may be, for example, a vial or the reservoir of a syringe. This also applies to all the other aspects of the invention described hereinafter.

The vaccine composition may be liquid or solid, e.g. lyophilized. A lyophilized composition may have the appearance of a powder. At the time of injection to a patient, the lyophilized composition is reconstituted with an appropriate pharmaceutical solution. This also applies to all the other aspects of the invention described hereinafter.

According to conventional practice in the art and for the purposes herein, it is understood that "antigen adsorbed" or "initially adsorbed" is not intended to mean that 100% of the antigen amount is actually adsorbed. These terms simply mean that a substantial amount of antigen is adsorbed. This also applies to all the other aspects of the invention described hereinafter.

As mentioned above, the device may be a plastic device made out of, for example, a chlorobutyl or bromobutyl polymer. This standard device is treated with a fluoropolymer; in particular, it may be submitted to a laminar flow treatment with a fluoropolymer, this laminar flow treatment being carried out on the entire device or, at the very least, on the surface of the device contactable with the composition. The laminar flow treatment makes it possible to deposit a very thin layer (e.g., film) of the fluoropolymer. As will be appreciated, the area of the coated surface may exceed the surface contactable with the composition. Indeed, in one embodiment, the whole surface of the device is coated with the fluoropolymer.

For use in the present invention, the fluoropolymer may be, for example, polytetrafluoroethylene (PTFE), polytetrafluoropropylene (PTFP), fluorinated ethylene propylene (FEP, a copolymer of hexafluoropropylene and tetrafluoroethylene), polychlorotrifluoroethylene (PCTFE), perfluoroalkoxy co-polymer (PFA), poly(ethylene-co-tetrafluoroethylene) (ETFE), poly(ethylenechlorotrifluoroethylene) (ECTFE), polyvinyl fluoride (PVF) or polyvinylidene fluoride (PVPF).

The method/use disclosed herein makes it possible to reduce the desorption speed of the antigen adsorbed on the aluminum adjuvant and/or the desorption percentage (or desorption rate) after a defined storage time at a given temperature. The desorption rate may be expressed as follows: (amount of non-adsorbed antigen)/(total antigen amount present in the composition). Typically, the desorption rate can be assessed by centrifuging the vaccine composition (samples at T (time)=0 and at the end of the experiment); recovering the supernatants which contain the desorbed antigen; and then quantifying the desorbed fraction by assaying the antigen in the supernatants and in the whole vaccine using a suitable method chosen according to the nature of the antigen. The desorption percentage (or desorption rate) can vary from one antigen to another according to the strength/weakness of the antigen-adjuvant interaction. Nevertheless, it is considered that the desorption percentage (or desorption rate) can be reduced by 10 to 15 or 20% compared with a standard loading method using standard stoppers—said reduction being measured 1 or 2 months after the date of loading. During this period of time, the storage is carried out at a temperature of +5 to 25° C. As may be easily appreciated, the adsorption percentage (adsorption rate) may be easily deduced from the desorption percentage (or desorption rate).

When the device is used not only to close the container but also to deliver the composition contained in the container, such as by sliding the plunger of a syringe, it is recommended to siliconize the inner surface of the container.

However, it has been observed that silicone may in some cases be detrimental to adsorption. Indeed, the desorption rate observed in compositions stored in syringes conventionally siliconized by mere surface-treatment with a silicone-in-water emulsion may be higher than the desorption rate observed in compositions stored in non-siliconized containers. We postulate that although the silicone adheres to the inner surface of the container, it remains in free form and, upon shaking or stirring, can flow away from the inner surface and pass into the container's content (the vaccine composition).

We have now found that this latter problem can be solved by using a container wherein the inner surfaces are coated with polymerized silicone. Such a container can be obtained by treating the inner surface of the container with a silicone-in-water emulsion, followed by heating the container, for example at a temperature of 270 to 330° C. for 30 min. Upon heating, the silicone polymerizes on the inner surface of the container and is therefore no longer capable of mixing with the composition. Polymerizing the silicone makes it possible to reduce the surface energy of the silicone to which the vaccine composition may be sensitive.

Additionally, the siliconizing operation comprising a polymerization step (i) is more precise and more homogeneous that a simple standard siliconizing operation; and (ii) makes it possible to reduce the amount of silicone that is used (that is, loaded on the inner surface of the container) by about a factor of 10 without any loss of lubricating effect. For example, according to a standard siliconizing process, from 400 to 1000 μg of silicone are deposited in a syringe intended to contain doses of 0.5-1 ml (the total inner surface of the 0.5-1 ml syringe reservoir is about 8 cm$^2$; in this example this surface corresponds to an amount of silicone of from about 50 to 125 μg/cm$^2$), whereas from 40 to 100 μg of silicone are sufficient for the same syringe (about 5 to 12 μg/cm$^2$) if silicone is deposited on the inner surfaces of the container and then polymerized, for example by heating. The fact that the inner surface of the syringe is coated with a low amount of polymerized silicone in a more homogenous manner than with a low amount of free silicone allows non-siliconized plungers to slide smoothly, whereas such plungers are inoperative with syringes coated with low amount of free silicone.

This is the reason why the invention also comprises a second method for reducing and/or slowing down the desorption of an antigen adsorbed on an aluminum adjuvant, the method comprising filling a container with a vaccine composition comprising the antigen adsorbed on the aluminum adjuvant, wherein the inner surface of the container is coated with polymerized silicone.

In other words, the invention also comprises a second method for loading and storing a vaccine composition containing an antigen adsorbed on the aluminum adjuvant, the method comprising filling a container with the composition wherein the inner surface of the container is coated with polymerized silicone.

In a similar manner, the invention also comprises the use of a container having an inner surface coated with polymerized silicone for storing a vaccine composition comprising an antigen adsorbed on an aluminum adjuvant.

Advantageously, the container having inner surfaces coated with polymerized silicone is made of plastic or glass. Advantageously, the container is the reservoir of a syringe.

The amount of polymerized silicone coated on the inner surface of the container is from 3 to 25 μg/cm$^2$; advantageously from 5 to 20 μg/cm$^2$; preferably from 5 to 15 μg/cm$^2$.

As may be easily understood, the container used in the first methods of the invention may be advantageously coated with polymerized silicone as described above.

In another aspect, the invention comprises:

A—A container (i) which contains a vaccine composition comprising an antigen adsorbed on an aluminum adjuvant; and (ii) which is closed by a device acting as a stopper, wherein the surface of the device contactable with the composition is coated with a fluoropolymer;

B—A container (i) having inner surfaces coated with polymerized silicone; and (ii) containing a vaccine composition comprising an antigen adsorbed on an aluminum adjuvant; and C—A container (i) having inner surfaces coated with polymerized silicone; (ii) containing a vaccine composition comprising an antigen adsorbed on an aluminum adjuvant; and (iii) which is closed by a device acting as a stopper, wherein the surface of the device contactable with the composition is coated with a fluoropolymer.

In other words, the invention relates to a vaccine composition comprising an antigen adsorbed on an aluminum adjuvant which is loaded into and stored in a container (i) having the inner surface coated with polymerized silicone; and/or (ii) which is closed by a device acting as a stopper, wherein at least the surface of the device contactable with the composition is coated with a fluoropolymer.

Vaccine compositions stored in containers according to the invention include:

A vaccine composition comprising an antigen, wherein the minimal antigen amount required for intended use (e.g., as a dose for administration to a human) is adsorbed on an aluminum adjuvant;

A vaccine composition comprising an antigen adsorbed on an aluminum adjuvant, wherein the vaccine composition when loaded in a container for use in the present invention, exhibits an adsorption percentage of at least:
  (a) 65-70% of the total antigen amount present in the composition, when, immediately after loading, the composition is stored at (i) 5±3° C. for 2-3 years; or (ii) 25±3° C. for 2-3 months; or
  (b) 80-90%, of the total antigen amount present in the composition, when, immediately after loading, the composition is stored at 5±3° C. for 18 months; and A vaccine composition comprising an aluminum adjuvant and an antigen able to adsorb onto the aluminum adjuvant, wherein the percentage of the antigen adsorbed on the aluminum adjuvant is at least 5 or 10% higher than the percentage observed when the same vaccine composition is contained in a standard container having uncoated inner surfaces or inner surfaces coated with non-polymerized silicone, the comparison between the antigen adsorption percentages being carried out after storage of the vaccine-containing containers at 25° C. for 2 months, starting from the date of filling the containers.

For the purposes of the present invention, the container may be any type of reservoir, such as vials or syringes, and may contain multiple doses (multidose container) or a single dose (single-dose container). As an example, the container may be a syringe or a part of a syringe comprising the reservoir containing the vaccine closed by a device acting as a stopper and as a system for releasing the vaccine at the time of administration (e.g., using a plunger). The device acting as a stopper may be a plunger.

Stoppers and/or plungers for use in the present invention are sold, for example, by Helvoet Pharma (Omniflex™ technology) and by West Pharma (Fluorotec™ technology). Glass syringe reservoirs coated with polymerized silicone for use in the present invention are sold, for example, by Nuova Ompi srl, Becton-Dickinson and Gerresheimer (Baked-on technology).

The antigen and the aluminum adjuvant may be any antigen and any aluminum adjuvant provided, of course, that they are both capable of interacting with each other. Furthermore, it may easily be understood that the present invention is of particular interest for an antigen-aluminum adjuvant pair having a relatively weak interaction force; the interaction force possibly depending on the environment. This interaction force can be assessed according to a variety of tests. For example, an aluminum adjuvant may be used to form various antigen-adjuvant pairs (the antigen varies from one pair to the other, the adjuvant remaining the same). Then a large amount of a compound able to compete with the antigen for the interaction with the adjuvant is added. The various preparations are centrifuged and the supernatants recovered. Finally, the amount of antigen desorbed is assayed in the supernatants, and as a result, antigens may be compared for their interaction force with the adjuvant.

A relatively weak interaction force is an interaction force that leads to an adsorption that may be detrimentally affected by a standard filling with the composition containing the antigen-aluminum adjuvant complex. Various elements involved in the manufacture of a container, such as, for example, latex, antioxidants, silicone and metal ions (e.g., zinc and tungsten), can destabilize the antigen-adjuvant complex.

By "adsorption" it is generally meant any phenomenon aimed at forming an antigen-adjuvant complex involving i.a. electrostatic interaction forces, hydrophobic interactions or ligand exchange. Thus, the antigen may be attached to the surface of the network of the aluminum adjuvant or embedded inside after co-precipitation with the aluminum adjuvant.

For use in the present invention, an aluminum adjuvant may be aluminum oxy hydroxide (AlOOH), such as the product sold by Brenntag AG (Superfos) or Reheis Corp.; and aluminum hydroxy phosphate ($AlOHPO_4$), such as the product sold by Alphos.

For a vaccine composition to be effective, the minimal antigen amount required for adsorption onto the aluminum adjuvant essentially depends upon the antigen itself, and is readily determinable by those of ordinary skill in the art.

In a particular embodiment, the antigen can be the hepatitis B surface antigen (HBsAg). It is particularly advantageous to adsorb HBsAg onto AlOOH as HBsAg exhibits an iso electric point (IEP) less than 7 (about 4 to 5) and AlOOH exhibits a point of zero charge (PZC) greater than 7 (about 9 to 11).

The vaccine composition for use in the present invention can contain one or more antigen(s), at least one of them being adsorbed on the aluminum adjuvant and it being possible for the others to be adsorbed as well or not.

According to one embodiment, the composition for use in the present invention comprises HBsAg adsorbed on AlOOH (AlOOH-HbsAg complex) and a second antigen, which is polyribosylribitol phosphate (PRP) of *Haemophilus influenzae* (HiB valence), preferably in a form conjugated to a carrier protein (C) which may be i.a. Dt or Tt.

According to another particular embodiment, when the antigen adsorbed on the aluminum adjuvant is HBsAg, the vaccine composition may also contain, as additional antigens, one or more of the following: diphtheria toxoid (Dt) (diphtheria valence); tetanus toxoid (Tt) (tetanus valence); *Bordetella pertussis* detoxified toxin (Ptdx), fimbriae, filamentous haemagglutinin (FHA) and/or pertactin (69 kD antigen) (*pertussis* valence); inactivated poliovirus serotype 1, 2, or 3 (polio valence); and polyribosylribitol phosphate (PRP) of *Haemophilus influenzae* (HiB valence), preferably in a form conjugated to a carrier protein (C) which may be i.a. Dt or Tt.

As a matter of example, the composition may comprise HBsAg, Dt, Tt, Pt and FHA adsorbed on AlOOH (the AlOOH-HbsAg-Dt-Tt-Pt-FHA complex), the polio valence, and PRP-C substantially non-adsorbed on AlOOH.

In a general manner, the invention is also particularly advantageous when the vaccine composition comprises several valences, for example 2, 3, 4, 5, 6 or more, each represented by one or more antigens (2, 3, 4 or 5), several antigens being adsorbed on the aluminum adjuvant. Indeed, under the standard filling mode, the higher the number of antigens/valences adsorbed on the aluminum adjuvant, the more critical is the phenomenon of destabilization by the container. The antigen-adjuvant interaction force often differs from one antigen to another and, in a composition containing several antigens, the antigen with the weakest interaction force exhibits the highest tendency to desorb under adverse conditions.

Examples and Experimental Results

A—A bulk of a vaccine composition containing the hepatitis B surface antigen, diphtheria toxoid, tetanus toxoid, and pertussis valence, each adsorbed on aluminum oxy hydroxyde, as well as the polio and non-adsorbed Haemophilus influenzae B (HiB) valences was distributed into three categories of single-dose syringes, the characteristics of which were as follows:
  (1) standard siliconized glass syringes with standard stopper/plunger made of non-laminated plastic;
  (2) standard siliconized glass syringes with fluoropolymer-coated stopper/plunger (West Pharma; Fluorotech™ technology); and
  (3) syringes, the inner surface of which is coated with polymerized silicone (Baked-on syringe system Luercone™ from Gerresheimer) with fluoropolymer-coated stopper/plunger (West Pharma; Fluorotech™ technology).

The bulk was distributed in 0.5 mL single doses, each dose containing 10 µg of HBsAg, 30 Lf of Dt, 10 Lf of Tt, 25 µg of Pt, 25 µg of FHA, 40 DU (Antigen D Unit) of IPV1, 8 DU of IPV2, 32 DU of IPV3, 12 µg of PRP (in PRP-Tt conjugate form), 0.6 mg of Al, 55 mM of phosphate ions, 20 mM of carbonate ions, and Tris sucrose buffer, 2.5 mM, 2.125%, at pH 6.8-7.2.

All the syringes of the three categories were stored horizontally at 25° C. for two months (accelerated ageing). The HBsAg desorption was measured in each of the three categories at T=0 (just after loading the syringes) and then after two months.

Desorption was evaluated by centrifuging the content of the syringes and then measuring the amount of desorbed HBsAg present in the supernatant by ELISA (sandwich ELISA, involving a mouse anti-HBsAg monoclonal antibody (IgM) for coating and capture, a second mouse anti-HBsAg monoclonal antibody (IgG) and a third anti-mouse IgG polyclonal antibody coupled to peroxydase (Sigma, Ref. A3673) which is revealed by adding tetramethyl benzidine).

At T (time)=0, the HbsAg adsorption level was identical in the three categories (98% of the total HBsAg was adsorbed). At T=2 months, desorption was observed in all the categories, but the desorption percentage differed depending upon the category. The highest desorption percentage was found in category (1) (At T=1 and 2 months, 55 and 50% of the total HBsAg was adsorbed, respectively), whereas the lowest percentage was found in category (3) (At T=1 and 2 months, 72 and 69% of the total HBsAg was adsorbed, respectively).

B—A bulk of the vaccine composition described in A—was distributed into two categories of single-dose 1 mL syringes, the characteristics of which were as follows:
  (1) standard siliconized glass syringes (free silicone); and
  (2) non-siliconized syringes.

The bulk was distributed in 0.5 mL single doses, each dose containing 10 µg of HBsAg, 30 Lf of Dt, 10 Lf of Tt, 25 µg of Pt, 25 µg of FHA, 40 DU (Antigen D Unit) of IPV1, 8 DU of IPV2, 32 DU of IPV3, 12 µg of PRP (in PRP-Tt conjugate form), 0.6 mg of Al, 55 mM of phosphate ions, 20 mM of carbonate ions, and Tris sucrose buffer, 2.5 mM, 2.125%, at pH 6.8-7.2.

All the syringes of the two categories were stored vertically at 25° C. for two months (accelerated ageing). The HBsAg desorption was measured in each of the two categories at T=0 (just after filling syringes) and then after two months, as described in A—above.

At T (time)=0, the HbsAg adsorption level was identical in the two categories (98% of the total HBsAg was adsorbed). At T=2 months, desorption was observed in all the categories, but the desorption percentage differed depending upon the category. The highest desorption percentage was found in category (1) (At T=1 and 2 months, 69 and 68% of the total HBsAg was adsorbed, respectively), whereas the lowest desorption percentage was found in category (2) (At T=1 and 2 months, 73% of the total HBsAg was adsorbed). This clearly indicates that the antigen adsorption onto an aluminum adjuvant is sensitive to free silicone.

C—A bulk of the vaccine composition described in A—was distributed into three types of single-dose 1 mL syringes, the characteristics of which were as follows:
  (1) low siliconized glass syringes (50-100 µg free silicone/syringe);
  (2) standard highly siliconized glass syringes ((RTF syringe Luercone™ from Gerresheimer): 800 µg to 1 mg free silicone/syringe); and
  (3) syringes having inner surface coated with polymerized silicone (50-100 µg/syringe).

Syringes of category (1) are operative only if the plunger used for injection is also siliconized, because the amount of silicone coating the inner surface of the syringe is too low to allow sliding on its own.

All the syringes (types 1 to 3) were closed with the same type of non-siliconized stopper.

The bulk vaccine was distributed in 0.5 mL single doses, each dose being as described in A and B.

All the syringes of the three types were stored vertically at 25° C. for two months (accelerated ageing). The HBsAg desorption was measured in each of the three types at T=0 (just after filling syringes) and then after two months, as described in A—above.

At T (time)=0, the HbsAg adsorption level was identical in the three types (94% of the total HBsAg was adsorbed). At T=2 months, desorption was observed in all syringes, but the desorption percentage differed depending upon the type. The highest desorption percentage was found in type (2) (At T=1 and 2 months, 60 and 58% of the total HBsAg was adsorbed, respectively), whereas the desorption percentage was found similar in types (1) and (3) and definitively much lower than in type (2): In type (1), at T=1 and 2 months, 73% and 68% of the total HBsAg was adsorbed, respectively. In type (3), at T=1 and 2 months, 69% and 66% of the total HBsAg was adsorbed, respectively.

Again, this clearly indicates that (i) the antigen adsorption onto an aluminum adjuvant is sensitive to free silicone loaded in an amount necessary for sliding and (ii) polymerization of silicone allows overcoming this issue.

D—A stability study has been conducted at 5±3° C. for 18 months with the filled syringes described in A—(3). At least 80-90% of the total HBsAg was still adsorbed at the end of the 18-month period.

What is claimed is:

1. A vaccine comprising a container containing a liquid multivalent vaccine composition comprising hepatitis B surface antigen adsorbed on aluminum oxyhydroxide, wherein the container (i) has inner surfaces coated with polymerized silicone; and (ii) is closed by a device acting as a stopper, wherein the surface of the device contactable with the vaccine composition is coated with a fluoropolymer, wherein the vaccine composition has reduced desorption rate of hepatitis B as compared to an otherwise identical vaccine composition stored in a standard container not having inner surfaces being coated with polymerized silicone and/or closed by a device coated with the said fluoropolymer.

2. The vaccine as claimed in claim 1, wherein the fluoropolymer is selected from the group consisting of polytetrafluoroethylene (PTFE), polytetrafluoropropylene (PTFP), fluorinated ethylene propylene (FEP, a copolymer of hexafluoropropylene and tetrafluoroethylene), polychlorotrifluoroethylene (PCTFE), perfluoroalkoxy co-polymer (PFA), poly(ethylene-co-tetrafluoroethylene) (ETFE), poly(ethylenechlorotrifluoroethylene) (ECTFE), polyvinyl fluoride (PVF) and polyvinylidene fluoride (PVPF).

3. The vaccine as claimed in claim 1, wherein the container is a syringe and the device acting as a stopper is a plunger.

4. The vaccine as claimed in claim 1, wherein the percentage of the hepatitis B adsorbed on the aluminum adjuvant is at least 5% higher than that of the otherwise identical vaccine composition stored in the standard container, when storage is carried out at 25° C. for 2 months from date of filling.

5. The vaccine as claimed in claim 1, wherein the desorption rate is reduced by 10% or more as compared to an otherwise identical vaccine composition stored in the standard container, when storage is carried out at 5-25° C. for 1 or 2 months from date of filling.

6. The vaccine as claimed in claim 1, wherein the inner surfaces of the container are coated with polymerized silicone at an amount from 3 to 25 μg/$cm^2$.

7. The vaccine as claimed in claim 1, wherein the vaccine composition further comprises additional antigens selected from one or more of diphtheria toxoid (Dt) (diphtheria valence); tetanus toxoid (Tt) (tetanus valence); *Bordetella pertussis* detoxified toxin (Ptdx), fimbriae, filamentous haemagglutinin (FHA) and/or pertactin (69 kD antigen) (*pertussis* valence); inactivated poliovirus serotype 1, 2, or 3 (polio valence); or polyribosylribitol phosphate (PRP) of *Haemophilus influenzae* (HiB valence).

8. The vaccine as claimed in claim 1, wherein the vaccine is a single-dose vaccine.

9. The vaccine as claimed in claim 8, wherein each single-dose comprises 10 μg of hepatitis B surface antigen.

10. The vaccine as claimed in claim 7, wherein each single-dose comprises 0.6 mg aluminum adjuvant.

11. The vaccine as claimed in claim 2, wherein the fluoropolymer is poly(ethylene-co-tetrafluoroethylene) (ETFE).

12. The vaccine as claimed in claim 2, wherein the fluoropolymer is polytetrafluoroethylene (PTFE).

13. A vaccine comprising a container containing a liquid vaccine composition comprising hepatitis B surface antigen adsorbed on an aluminum adjuvant, wherein the container (i) has inner surfaces coated with polymerized silicone at an amount from 3 to 25 μg/$cm^2$; and (ii) is closed by a device acting as a stopper, wherein the surface of the device contactable with the vaccine composition is coated with a fluoropolymer, wherein the vaccine composition has reduced desorption rate of hepatitis B as compared to an otherwise identical vaccine composition stored in a standard container not having inner surfaces being coated with polymerized silicone and/or closed by a device coated with the said fluoropolymer.

* * * * *